US007066598B2

(12) United States Patent
Niven

(10) Patent No.: US 7,066,598 B2
(45) Date of Patent: Jun. 27, 2006

(54) EYE MODEL FOR MEASUREMENT

(75) Inventor: Gregg D. Niven, Kaysville, UT (US)

(73) Assignee: Bausch & Lomb Incorporated, Rochester, NY (US)

( * ) Notice: Subject to any disclaimer, the term of this patent is extended or adjusted under 35 U.S.C. 154(b) by 461 days.

(21) Appl. No.: 10/397,097

(22) Filed: Mar. 25, 2003

(65) Prior Publication Data

US 2004/0189934 A1     Sep. 30, 2004

(51) Int. Cl.
*A61B 3/10*     (2006.01)
*A61B 3/00*     (2006.01)
*G09B 23/28*     (2006.01)
(52) U.S. Cl. .................. 351/205; 351/200; 351/203; 434/271
(58) Field of Classification Search .................. 351/205
See application file for complete search history.

(56) References Cited

U.S. PATENT DOCUMENTS

| 4,865,552 | A | 9/1989 | Maloney et al. ............ 434/271 |
| 5,652,640 | A | 7/1997 | Schneider et al. .......... 351/205 |
| 5,893,719 | A | 4/1999 | Radow ........................ 434/271 |
| 6,485,142 | B1 | 11/2002 | Sheehy et al. .............. 351/203 |
| 6,626,535 | B1* | 9/2003 | Altmann ..................... 351/177 |
| 2002/0085172 | A1 | 7/2002 | Altmann ..................... 351/178 |
| 2003/0038934 | A1* | 2/2003 | Baske et al. ................ 356/246 |

FOREIGN PATENT DOCUMENTS

WO     WO 03/016855 A1     2/2003

* cited by examiner

*Primary Examiner*—Patricia Bianco
*Assistant Examiner*—John R. Sanders

(57) ABSTRACT

An eye model 10 includes a partially-spherical transparent disk 12 for representing a cornea, and a housing 14 attached to the disk 12 including a volume for holding a fluid representing aqueous within an eye. An annular ring 18 is attached to the housing 14 for representing an iris and a lens 20 is attached to the annular ring 18 for representing a lens of the eye. An end-cap 22 on an end opposite the disk 12 represents a retina.

10 Claims, 2 Drawing Sheets

EYE MODEL FOR MEASUREMENT

BACKGROUND OF THE INVENTION

1. Field of the Invention

The present invention is directed to an eye model. Specifically, the present invention is directed to an eye model for measurement by an ophthalmic diagnostic instrument for calibration and development purposes.

2. Description of Related Art

A difficulty in the development of ophthalmic diagnostic devices is obtaining information about the human eye, such as geometry, aperture diameter depth, etc. without incurring significant discomfort or injury to a human subject. The development of an ophthalmic diagnostic instrument requires repetitive gathering of information, and this can be painful and problematic for a human test subject.

An additional problem is the fact that the eye is a living organism and differs from one person to the next. Obviously, this compounds the problem of gathering accurate data about the eye geometry because there is no way to truly measure in-vivo tissue of the eye to the micron level without physically removing the eye.

Therefore, to develop an ophthalmic diagnostic instrument and to gather the information needed for the device development, artificial representations of the human eye have been developed. These artificial representations range from simple meniscus shapes filled with fluid to complex multiple part assemblies. One design that has been used as a spherical meniscus shape attached to an acrylic plate. The shape behind the meniscus is back-filled with a fluid that represents aqueous found in the human eye. The fluid is used to lower the reflection from the rear surface of the meniscus. Typically, these eye models do not incorporate the iris and lens into the model.

A common drawback to these types of assemblies, is the problem of evacuating air from behind the meniscus and keeping the air from entering the chamber and preventing fluid from escaping from the chamber. Air entering the artificial models then presents itself within the area to be measured by the diagnostic instrument. These air bubbles optically distort the information to be gathered and also disrupts the visual field thereby, preventing clean images of the surface from being obtained.

Therefore, it would be desirable to have a new eye model which overcomes these drawbacks and assures that fluid fills the chamber covering the area to be measured and sufficiently evacuates the air and prevents the air from migrating back into the chamber.

DETAILED DESCRIPTION OF THE PREFERRED EMBODIMENT

Figure 1:
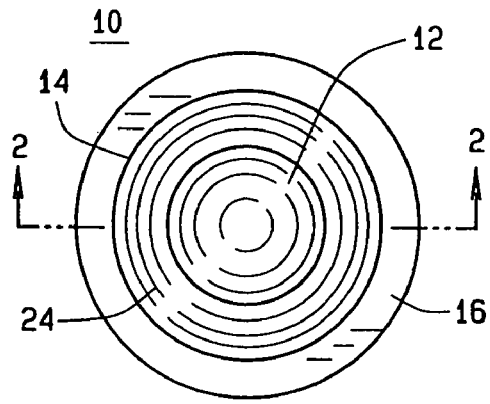
FIG. 1 is a top view of an eye model in accordance with the present invention.

FIG. 1 shows a top view of an eye model 10 for use with a diagnostic measurement system (not shown). Eye model 10 includes a partially-spherical shaped transparent disk 12 representing a cornea attached to a housing 14. Housing 14 includes a volume for holding a fluid representing the aqueous within the eye. Eye model 10 also preferably includes a flange 16 that helps in handling as well as providing an additional method of preventing air bubbles from migrating to the area under the transparent disk 12.

Figure 2:
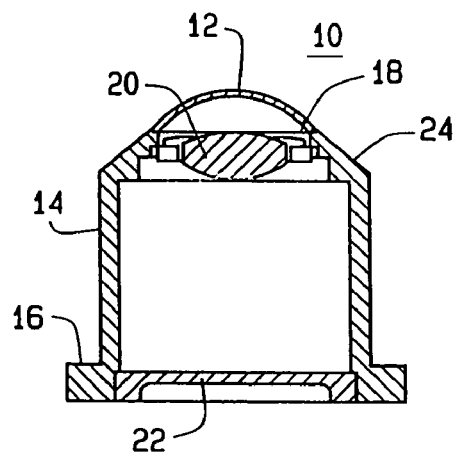
FIG. 2 is a side elevation view of FIG. 1 taken along line 2—2.

FIG. 2 shows a cut-away view of the eye model of FIG. 1 including the disk 12 and housing 14. In addition, the eye model includes an annular ring 18 attached to the housing 14 representing an iris and a lens 20 attached to the annular ring 18 representing the crystalline lens of an eye. In addition, an end-cap 22 is on an end opposite the disk 12 and represents a retina when permanently attached in place and prior to attachment provides access for filling the chambers with fluid.

Preferably, disk 12 is a PMMA (polymethyl methacrylate) machined meniscus disk coped with boron nitride or some other dopant in order to approximate the light scatter normally found in a human cornea. though other suitable materials may also be used. Preferably, disk 12 is machined to sizes used on prior art models and is sized to allow equipment polishing and can be made on traditional contact lens lathes so that the disk 12 is free from scratches or imperfections associated with normal machined and polished disks. Disk 12 is preferably attached to housing by a compatible cement or plastic solvent that provides a liquid and air proof bond between the surfaces.

Housing 14 is preferably formed of a white acrylic or PMMA material thereby, representing the sclera of the eye. Also preferably, the angle of housing 14 at the disk 12 end shown at 24 is preferably an angle that is tangent to the disk 12. By having this angle, it is cheaper to make housing 14 than machining a continuous curved surface onto housing 14, although obviously a curved surface could be made. However, it is believed that acceptable measurements can be made using the angled surface 24 shown in FIG. 2.

Figure 3:
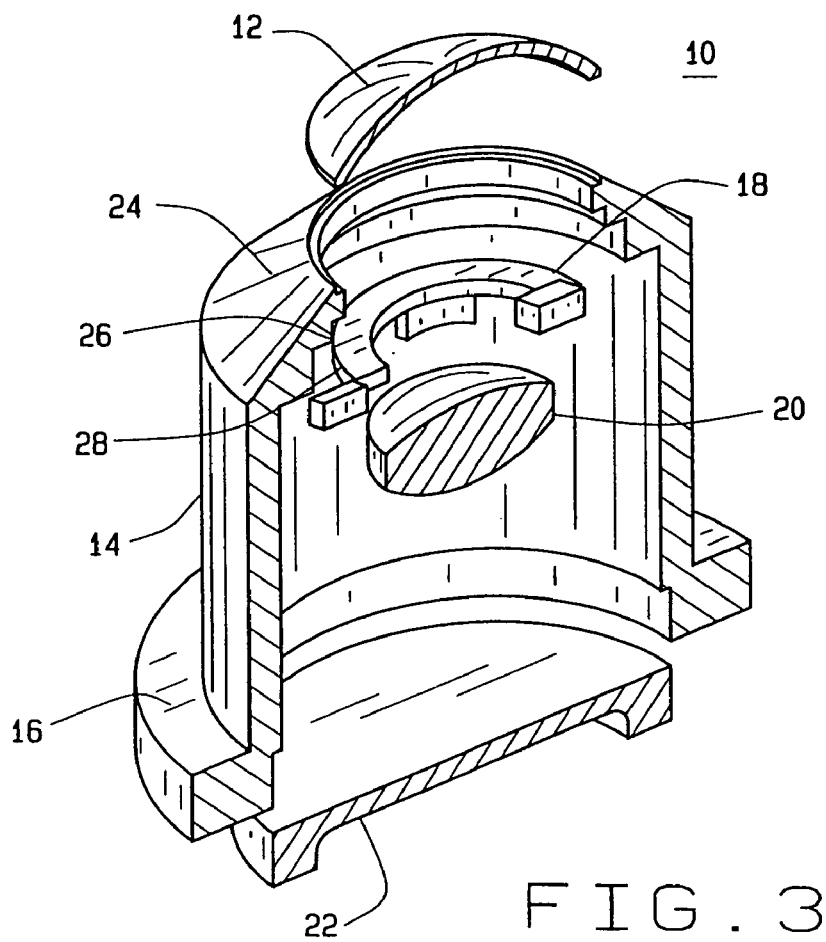
FIG. 3 is a cut-away exploded perspective view.

The annular ring 18 best seen in FIG. 3 represents the iris of a model and is preferably curved, as shown, to represent the iris-lens interface. The front surface 26 is preferably rough in texture to more accurately represent the iris, which is not smooth in the human eye. An annular edge 28 of the ring 18 should be spaced away from the edge of housing 14. This gap which is preferably about 0.5 millimeters, provides an exit path for air bubbles that may be trapped during filling of the model. Preferably, the model 10 is placed in a centrifuge (not shown) with disk 12 at the bottom. When the centrifuge is activated air will be forced from in front of ring 18 and be displaced by the fluid otherwise filling housing 14.

The lens 20 is preferably a doped acrylic for representing the actual refractive capability and light scatter of a lens of a human eye. The main function of lens 20 is for use in measurements using ultrasound and optical tomography devices. The doping in the lens 20 aids in visualizing its presence in the optical measurements. End-cap 22 represents a retina and therefore is preferably made of orange acrylic. End-cap 22 could be placed at the correct distance if the lens and aqueous used in the model are items with the correct refractive index which would allow use of the device with auto-refracting or wave-front measuring devices. The End-cap 22 could also be formed with a semi-circular surface that could represent the curved retina of an eye.

In use, eye model 10 is filled with suitable fluids to represent the aqueous/vitreous humor of an eye which fills the space between the disk 12 and the ring 18, and the chamber between the lens and retina portions of the model. The use of the appropriate fluid allows fluid to model light interfaces to approximate those liquid to tissue interfaces of the human eye. Any air that is be trapped in the chamber between disk 12 and iris 18 during filling of the housing 14 with fluid, will pass between the gap formed between ring 18 and housing 14, so that no air bubbles will be visible within the area of disk 12 to be measured, as described above. Housing 14 may be filled with fluid prior to fitting and cementing of end-cap 22 or through some other inlet formed in housing 14 that could be capped and sealed to prevent leakage. It is desirable to have very little air remain in the chamber 32 but some is helpful to prevent damage during shipment and use at various altitudes as the air can expand and compress easily to preventing damage to the housing 14 or the cemented joints between parts due to excessive pressure.

Figure 4:
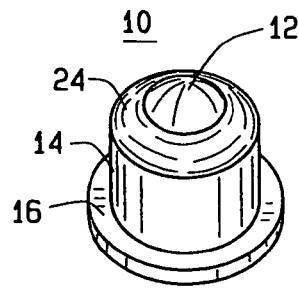
FIG. 4 is a perspective view of the eye model in accordance with the present invention.

FIG. 4 shows a perspective view of the eye model 10 fully assembled.

Figure 5:
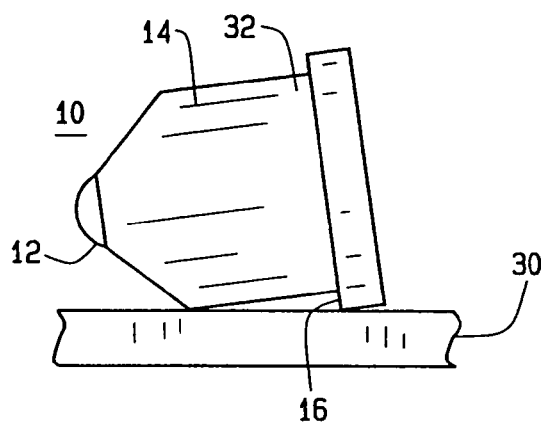
FIG. 5 is a side view of the eye model placed on a counter top.

FIG. 5 shows the utility of the flange 16 of the eye model 10. By placing the eye model 10 on a table or counter top 30, as shown, flange 16 adjacent, the end-cap 22 prevents air bubbles from migrating to the space between the disk 12 and the ring 18 when the model is placed on its side as shown. The present design prevents this because the disk 12 is in a lower position then the rear corner of the housing shown at 32 which is where any trapped air that may be present will accumulate. This flange 16 also helps to prevent the unit from rolling onto the floor by making the model roll in a circular fashion due to the different radii of the parts of the housing. The flange could also have a cord section machined on the flange that would create a flat surface that could prevent the model from rolling at all.

Figure 6:
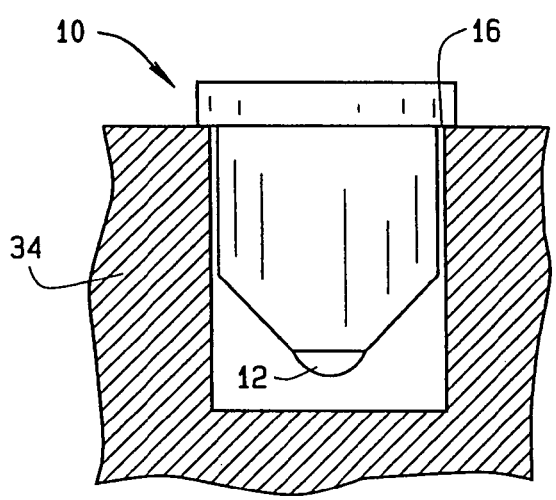
FIG. 6 is a view of the eye model being stored in a container.

In addition, FIG. 6 shows a preferred means of storing the eye model 10 in a container 34 shown in partial cut-away. Preferably, eye model 10 is suspended from flange 16 as shown with disk 12 at a bottom most point to prevent any air bubbles from accumulating in the cornea portion of the eye model.

Figure 7:
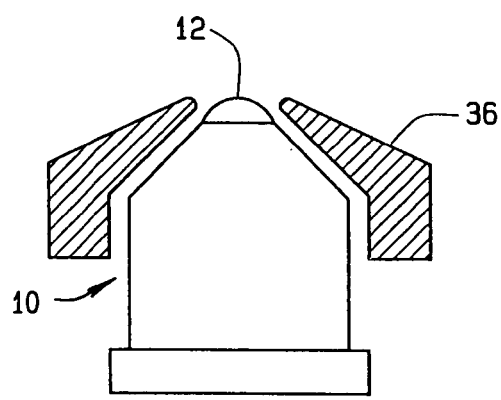
FIG. 7 shows a cut-away of an aperture placed over the eye model.

FIG. 7 shows an aperture 36 in partial cut-away placed over eye model 10. Preferably, the disk 12 is at least 12 millimeters in diameter or about 2 millimeters larger in diameter than a typical human eye. Therefore, the aperture 36 may be fit over an eye model 10 to limit the size of the cornea or disk 12 to be examined, as shown in FIG. 7. It is also possible for the aperture 36 to serve as a mount for the model in a device when being used for calibration of a diagnostic instrument.

I claim:

1. An eye model for use with diagnostic measurement systems comprising:
   a partially-spherical transparent disk for representing a cornea:
   a housing attached to the disk including a volume for holding a fluid representing aqueous within an eye;
   an annular ring attached to the housing for representing an iris;
   a lens attached to the annular ring for representing a lens of the eye;
   an end-cap on an end opposite the disk for representing a retina; and
   wherein the annular ring provides spacing between the ring and the housing for allowing air to escape from a space between the disk and the ring during filling of the housing with fluid.

2. An eye model for use with diagnostic measurement systems comprising:
   a partially-spherical transparent disk for representing a cornea;
   a housing attached to the disk including a volume for holding a fluid representing aqueous within an eye;
   an annular ring attached to the housing for representing an iris;
   a lens attached to the annular ring for representing a lens of the eye;
   an end-can on an end opposite the disk for representing a retina; and
   wherein the housing includes a flange adjacent the end-cap for preventing air bubbles from forming in a space between the disk and the ring when the model is placed on a side.

3. The model of claim 2 further including a storage unit, such that the model is suspended in the storage unit from the flange.

4. An eye model for use with diagnostic measurement systems comprising:
   a partially-spherical transparent disk for representing a cornea;
   a housing attached to the disk including a volume for holding a fluid representing aqueous within an eye and wherein at least a front portion of the housing is white for representing a sclera portion of the eye;
   an annular ring attached to the housing having a front rough-textured surface for representing an iris;
   a lens attached to the annular ring for representing a lens of the eye;
   an end-cap on an end opposite the disk for representing a retina having an orange surface facing the disk; and
   a flange adjacent the end-cap for preventing air bubbles from forming in a space between the disk and the ring when the model is placed on a side.

5. The model of claim 4, wherein the disk is formed of a PMMA material.

6. The model of claim 4, wherein the housing is formed of acrylic or PMMA material.

7. The model of claim 4, wherein spacing is provided between the ring and the housing for allowing air to escape from a space between the disk and the ring during filling of the housing with fluid.

8. The model of claim 4, wherein the lens is formed of an acrylic for representing a refraction of the eye.

9. The model of claim 4 further including a storage unit, such that the model is suspended in the storage unit from the flange.

10. The model of claim 4, wherein an aperture device fits over the housing to limit an area of the disk to be examined.

* * * * *